United States Patent [19]

Stowe et al.

[11] 3,934,151

[45] Jan. 20, 1976

[54] CHOPPER ASSEMBLY FOR X-RAY MACHINE

[76] Inventors: Ralph A. Stowe, 208 Frank, Joliet, Ill. 60435; Joseph W. Howe, 1446 N. Webster St., Naperville, Ill. 60540

[22] Filed: Aug. 14, 1974

[21] Appl. No.: 497,324

[52] U.S. Cl. .................................. 250/505; 250/511
[51] Int. Cl.² ........................................ G21K 1/04
[58] Field of Search ........... 250/511, 512, 513, 514, 250/505

[56] References Cited
UNITED STATES PATENTS
3,069,549  12/1962  Thompson .......................... 250/511

*Primary Examiner*—Craig E. Church
*Attorney, Agent, or Firm*—Leo J. Aubel

[57] ABSTRACT

A chopper assembly or shutter apparatus is disclosed for X-ray machines for controlling a chopper or shutter for selectively exposing the areas of a patient's body for obtaining X-ray photographs.

2 Claims, 7 Drawing Figures

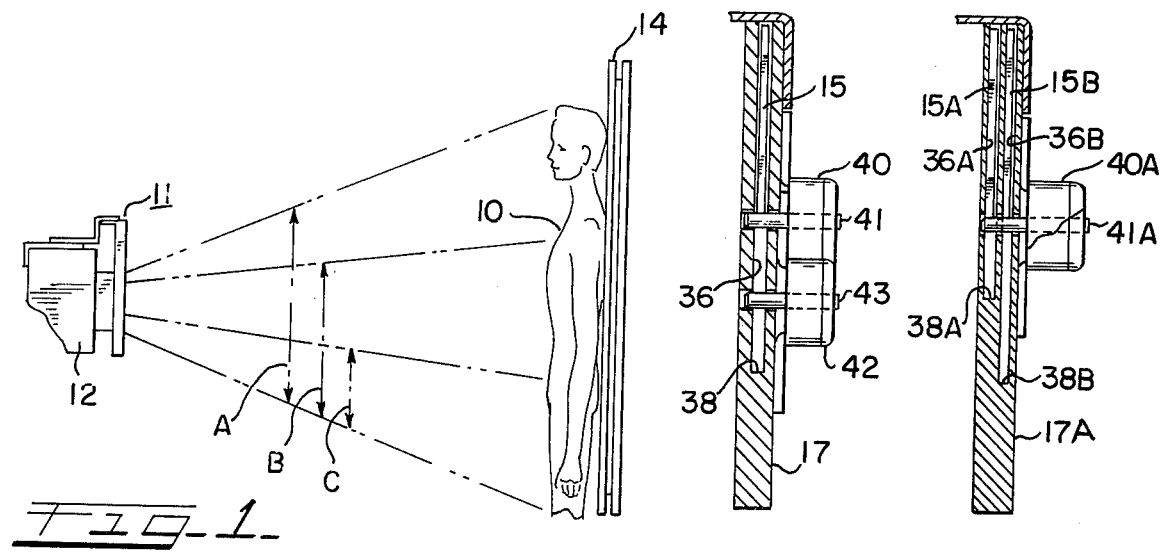
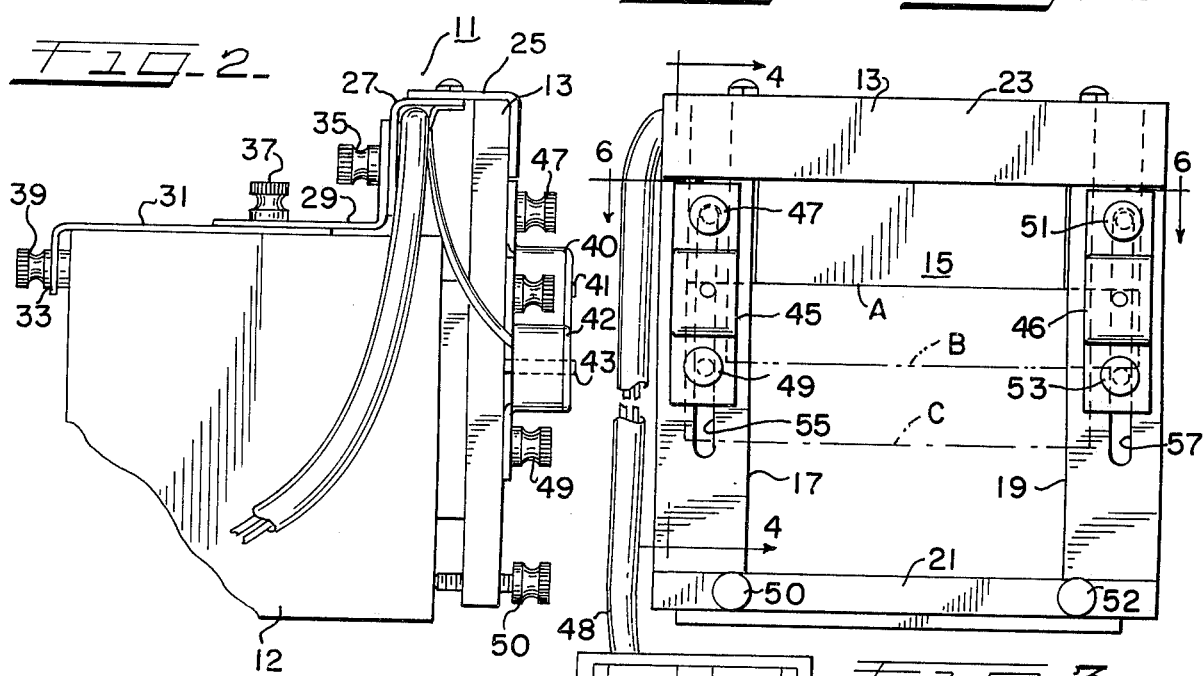
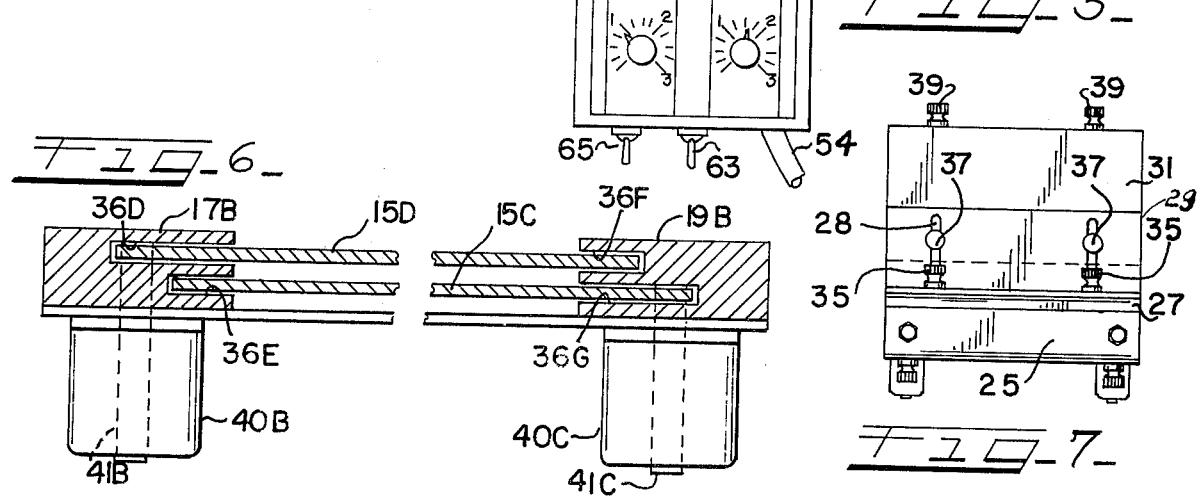

CHOPPER ASSEMBLY FOR X-RAY MACHINE

BACKGROUND OF THE INVENTION

The prior art shows various types of shutter apparatus and mounting arrangements for controlling the exposure of the patient's body to X-ray. Such examples of this art are U.S. Pat. Nos. 3,588,511; 3,069,549 and 3,048,700.

The present invention discloses an improved light chopper shutter apparatus for an X-ray machine including improved means for mounting and selectively moving the chopper mechanisms. One method of taking X-ray photographs consists of placing a patient in a standing or upright position for exposure to X-rays from a source spaced horizontally from the patient. The foregoing X-ray sources normally include means for collimating the beam such that the X-ray will tend to be parallel in a defined cone to penetrate the desired portion of the patient's body. The present invention is directed toward the use in this type of operation.

Certain problems have been experienced in obtaining clear and uniform X-ray pictures of a patient's body such as along the spinal column because of the differences in the size and density of the body areas along the spinal column.

An advantage of the present invention is that it provides shutter assembly for use with an X-ray source or machine for selectively controlling the X-rays penetrating the patient's body to thereby time the exposure of different areas of the body to the X-rays.

An additional advantage of the present invention is to provide a means to prevent over exposure of the less dense portions of the patient's body while allowing proper exposure to X-rays to the larger or more dense portions.

Another advantage of the present invention is that it can be easily mounted on a conventional X-ray machine; it can easily be removed for subsequent operations and further it can easily be operated and manipulated by the X-ray technician.

The foregoing and other obejcts, features and advantages of the invention will be apparent from the following more particular description of a preferred embodiment of the invention, as illustrated in the accompanying drawings wherein:

DESCRIPTION OF THE DRAWINGS

FIG. 1 is a side elevation of the inventive chopper assembly mounted on an associated X-ray machine for use in making an X-ray photograph of a patient;

FIG. 2 is a more detailed view of the chopper assembly showing the brackets for mounting the chopper assembly on the associated X-ray machine;

FIG. 3 is a front view of the chopper assembly showing the chopper, and indicating the various stopped positions of the chopper;

FIG. 4 is a side view of a cross section of the chopper assembly useful in explaining the operation of the chopper unit;

FIG. 5 is a modification of the structure of FIGS. 1–4 wherein two choppers are employed, each of which choppers drop to a single selected position;

FIG. 6 is a top view of the structure of FIG. 5; and,

FIG. 7 is a top view of the inventive chopper assembly.

DESCRIPTION OF THE INVENTION

The chopper or shutter assembly 11 of the invention is shown in FIG. 1. Chopper assembly 11 is mounted on an X-ray machine 12 of any suitable known design and in the position shown, the X-rays are being suitably collimated and directed from the X-ray machine 12 to penetrate the patient's body 10 to expose a conventional photographic film indicated generally as 14. The chopper assembly 11 is mounted on the X-ray machine 12 by suitable mounting brackets as will be explained in more detail with reference to FIG. 2.

The shutter assembly 11, includes a chopper 15 which may be of lead, is approximately ⅜ inches thick, 4 inches in height and about 5 inches in width. The detail of the chopper assembly will be explained with reference to FIGS. 3 and 4 which provide, in conjunction with X-ray machines, controls to select three timing periods and the precisely selected areas of the patient's body which the X-rays penetrate.

As indicated in FIG. 1, the patient is positioned to receive the X-ray from the X-ray machine. As mentioned above briefly, and as is well known, suitable means are provided to properly collimate the X-ray toward the patient. The areas of the body which are to be exposed are first emperically selected dependent on the height and measurement of the patient as by a source of luminescent light which is directed to simulate the X-rays to irradiate the patient's body. The source of X-rays, the patient and the chopper assembly are thus arranged as desired.

In an initial position, the position of the chopper 15 allows the entire cone of the X-rays to penetrate the patient's body to impinge on the film 14, this is indicated by the arrowed line A in FIG. 1 and line A of FIG. 3. In a second position, chopper 15 of chopper assembly 11 is moved to a position to shield out or stop a portion of the X-rays and only the intermediate and lower portions of the patient's body receive the X-rays; this is indicated by the arrowed line B of FIG. 1 and line B of FIG. 3. In a third position, the chopper 15 is moved to another position to shield out a large portion of the X-rays and only the lower extremeties of the patient's body recieve the X-rays; this is indicated by the arrowed line C of FIG. 1 and line C of FIG. 3. Thus, by selectively moving and positioning the shutter 15, the X-ray energy penetrating a selected area of a patient's body can be properly controlled.

Referring to FIGS. 2 and 3, the chopper assembly 11 includes a vertical frame essentially in rectangular form including two upright or vertical arms 17 and 19 which are mounted in spaced horizontal position on a base member 21 and a top cross piece 23. The cross piece 23 includes a folded over or horizontal extending flange 25 as indicated in FIG. 2. flange 25 attaches through a suitable L-bracket 27 to an adjustable and a second, slidable L-bracket 29, which in turn, is connected to an extension bracket 31, which includes a downwardly extending flange 33 to engage a shoulder support of the X-ray machine 12. Referring to FIG. 7, bracket 29 includes elongated slots 28 therein for receiving suitable thumb bolts such as 35 and 37 for permitting relative positionable adjustment of the brackets 27, 29 and 31 on the X-ray machine 12. Thumb bolt 39 adjusts flange 22 against the X-ray machine. Thumb bolts 35, 37 and 39 thus provide a means of conveniently securing and releasing the bracket from the X-ray machine. Note also thumb bolts 50 and 52 (FIG. 3) which extend through base member 21 to abut against the X-ray machine 12 to permit vertical canting and thus vertical positioning of the chopper assembly 11.

Solenoids 40 and 42 of conventional construction and operation are mounted on frame 13 by respective adjustable brackets 45 and 46 which may be secured in position by suitable bolts 47, 49, 51 and 53. Elongated slots 55 and 57 in the arms 17 and 19 of frame 13 permit vertical adjustment of brackets 45 and 46. Solenoids 40 and 42 each include electrically actuated plungers 41 and 43 which extend through respective slots 55 and 57 in arms 17 and 19. Plungers 41 and 43 position, that is stop downward movement of the chopper 15 in selectively controlled sequence as will be explained.

The solenoids 40 and 42 are connected to be actuated in time sequence through suitable known electrical connectors 48 by a time clock means of any suitable known electrical design, generally labeled 60, which clock means can be manually adjusted by suitable known controls for the desired time sequences. For example, time clock 60A controls solenoid 40 and time clock 60B controls solenoid 42. Time clock 60 is connected in series through lead 54 with the on-off switch of the X-ray source such that the time sequence for actuating the chopper is initiated when the X-ray source is directed to the patient; that is, zero reference time for applying the X-rays to the patient would be zero time reference for the time clock 60. In addition to the foregoing, time clock 60 includes a by-pass switch 65 such that the timing sequence can be initiated manually by the operator, as desired.

Refer now to FIG. 4. A vertical slot or guideway 36 is formed in arm 17. The chopper 15 is mounted for vertical movement in the guideway 36 and when solenoid 40 is actuated plunger 41 is moved outwardly (to the right) from the position shown in arm 17 permitting chopper 15 to drop, due to gravity, to a position supported by plunger 43 of solenoid 42. The time period during which chopper 15 is in a position shown in FIG. 4 after the X-rays are initiated is determined by clock 60A. The period of time during which chopper 15 is supported by plunger 43 is determined by clock 60B; that is, clock 60B determines the instant at which solenoid 42 is energized to withdraw plunger 43, and permit chopper 15 to fall to its stop 38. At a time period determined by the clock settings on the X-ray machine, the X-ray source will be turned off. The timing sequence is set by the operator in accordance with standard calculation techniques.

After the X-rays are turned off the operator manually lifts the chopper 15 to its initial position to ready the assembly for subsequent operations.

Note that in the present system, X-rays are provided to the patient's body in a given time interval, and the chopper 15 merely interrupts or shields portions of the patient's body from the X-rays.

FIG. 5 shows a modification of the inventive structure wherein a pair of choppers 15A and 15B are mounted in respective guideways 36A and 36B in arm 17A and identical guideways, not shown, and the corresponding opposite arms. In this modification, the plunger 41A extends through the frame to provide a stop for chopper 15A as well as stop for chopper 15B. Upon actuation of the solenoid 40A determined by clock 60A, solenoid plunger 41A is caused to be withdrawn to an intermediate position permitting shutter 15A to drop its top position at 38A. Upon the second or subsequent actuation of solenoid 40A determined by clock 40B, plunger 41A is withdrawn to its second position to permit chopper 15B to drop to its stop position 48B. In this manner, the same result is obtained as obtained for FIG. 4.

FIG. 6 shows still another modification of the inventive structure wherein two choppers 15C and 15D are employed. The choppers are mounted in respective guideways 36D and 36E in arm 17B and in guideway 36F, and 36G and arm 19B. As can be appreciated from FIG. 6, the movement of chopper 36D is controlled by solenoid 40B and plunger 41B and solenoid 40C and plunger 41C. Upon actuation of solenoid 41B, chopper 15D is caused to drop to a position and upon actuation of solenoid 40C, plunger 41C is withdrawn to permit chopper 15C to drop to its desired position.

Note that in each of the various embodiments, the stop position of the chopper is completely adjustable which renders the invention extremely convenient and useful.

While the invention has been particularly shown and described with reference to preferred embodiments thereof, it will be understood by those skilled in the art that various changes in form and details may be made therein without departing from the spirit and scope of the invention.

What is claimed is:

1. An assembly for use in operating conjunction with an X-ray machine for obtaining X-ray photographs of a patient, a chopper subassembly comprising a frame mountable between the source of X-ray of the machine and the patient, said frame including an opening therein for permitting the X-rays to pass therethrough, at least two vertically movable chopper plates each slidably mounted for selectively covering a portion of said opening, said chopper plates movable downwardly by gravity, movable stop means comprising solenoids with each solenoid controlling and stopping downward movement of a respective chopper plate at least two time clocks electrically connected with the X-ray machine, said solenoids being respectively controllable by said clocks and said clocks being operable in conjunction with the machine to controllably actuate said solenoids to control the movement and positioning of said chopper plates.

2. An assembly as in claim 1 wherein said solenoids each have a plunger selectively movable in response to the settings on said time clocks to control said chopper plates at distinct time periods.

* * * * *